US010426554B2

(12) United States Patent
Siewerdsen et al.

(10) Patent No.: US 10,426,554 B2
(45) Date of Patent: Oct. 1, 2019

(54) SYSTEM AND METHOD FOR TRACKING AND NAVIGATION

(75) Inventors: Jeffrey H. Siewerdsen, Baltimore, MD (US); Yoshito Otake, Baltimore, MD (US); Russell H. Taylor, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 473 days.

(21) Appl. No.: 14/113,563

(22) PCT Filed: Apr. 30, 2012

(86) PCT No.: PCT/US2012/035839
§ 371 (c)(1),
(2), (4) Date: Oct. 23, 2013

(87) PCT Pub. No.: WO2012/149548
PCT Pub. Date: Nov. 1, 2012

(65) Prior Publication Data
US 2014/0049629 A1   Feb. 20, 2014

Related U.S. Application Data

(60) Provisional application No. 61/480,422, filed on Apr. 29, 2011.

(51) Int. Cl.
*A61B 34/20* (2016.01)
*A61B 6/00* (2006.01)
(Continued)

(52) U.S. Cl.
CPC ............ *A61B 34/20* (2016.02); *A61B 6/4441* (2013.01); *A61B 2034/2055* (2016.02);
(Continued)

(58) Field of Classification Search
None
See application file for complete search history.

(56) References Cited

U.S. PATENT DOCUMENTS 5,016,639 A * 5/1991 Allen ........................ A61B 6/12
600/414
5,676,673 A * 10/1997 Ferre ...................... A61B 34/20
606/130
(Continued)

OTHER PUBLICATIONS

International Search Report and Written Opinion of PCT/US2012/035839.
(Continued)

*Primary Examiner* — Katherine L Fernandez
*Assistant Examiner* — Yi-Shan Yang
(74) *Attorney, Agent, or Firm* — Venable LLP; Henry J. Daley

(57) ABSTRACT

A tracking and navigation system is provided. The system includes an imaging or treatment device, a tracker device, and a fiducial marker. At least part of the imaging or treatment device is movable relative to a patient. The tracker device is mounted on the imaging or treatment device and is movable therewith relative to the patient. The fiducial marker may be fixed relative to the patient to define a patient coordinate system. The fiducial marker is detectable by the tracker device to substantially maintain registration between the tracker device and the patient coordinate system. A tracking and navigation kit including the tracker device and at least one fiducial marker may also be provided, for example, for retrofitting to existing imaging or treatment devices.

20 Claims, 4 Drawing Sheets

(51) Int. Cl.
*A61N 5/10* (2006.01)
*A61B 90/00* (2016.01)

(52) U.S. Cl.
CPC . *A61B 2090/376* (2016.02); *A61B 2090/3983* (2016.02); *A61N 2005/1061* (2013.01)

(56) References Cited

U.S. PATENT DOCUMENTS

| | | | | |
|---|---|---|---|---|
| 6,050,724 | A * | 4/2000 | Schmitz | A61B 6/08 378/205 |
| 6,161,032 | A * | 12/2000 | Acker | A61B 5/06 324/207.11 |
| 6,720,876 | B1 * | 4/2004 | Burgess | G01S 5/0289 340/10.1 |
| 6,823,207 | B1 | 11/2004 | Jensen et al. | |
| 6,980,921 | B2 | 12/2005 | Anderson et al. | |
| 7,180,072 | B2 * | 2/2007 | Persi | G06T 7/33 250/349 |
| 7,344,307 | B2 | 3/2008 | Yatsenko et al. | |
| 7,497,621 | B2 | 3/2009 | Yatesenko et al. | |
| 7,660,623 | B2 | 2/2010 | Hunter et al. | |
| 2001/0004395 | A1 * | 6/2001 | McCrory | A61K 49/0409 378/162 |
| 2002/0133175 | A1 * | 9/2002 | Carson | A61B 19/52 606/130 |
| 2005/0245817 | A1 | 11/2005 | Clayton et al. | |
| 2006/0173269 | A1 * | 8/2006 | Glossop | A61B 5/06 600/407 |
| 2008/0118103 | A1 | 5/2008 | Pescatore et al. | |
| 2008/0172069 | A1 | 7/2008 | Dukesherer et al. | |
| 2008/0194948 | A1 * | 8/2008 | Fleig | A61B 19/54 600/426 |
| 2008/0317281 | A1 * | 12/2008 | Goldbach | G06F 19/3412 382/103 |
| 2009/0232282 | A1 * | 9/2009 | Belson | A61B 6/107 378/203 |
| 2010/0228340 | A1 * | 9/2010 | Erbel | A61F 2/88 623/1.18 |
| 2010/0286812 | A1 * | 11/2010 | Slettemoen | B23Q 17/09 700/160 |
| 2011/0087092 | A1 * | 4/2011 | Kienzle, III | A61B 6/02 600/424 |
| 2012/0035462 | A1 * | 2/2012 | Maurer, Jr. | A61B 6/5247 600/411 |
| 2012/0121124 | A1 * | 5/2012 | Bammer | G06K 9/3216 382/103 |
| 2012/0307021 | A1 * | 12/2012 | Tsai | G06T 7/55 348/50 |
| 2014/0049629 | A1 * | 2/2014 | Siewerdsen | A61B 19/5244 348/77 |
| 2016/0175064 | A1 * | 6/2016 | Steinle | A61B 90/39 600/424 |

OTHER PUBLICATIONS

Dawson et al., Advances in image-guided radiation therapy. J.Clin. Oncol. Mar. 10, 2007;25(8):938-946.
Gueziee et al., Anatomy-based registration of CT-scan and intraoperative X-ray images for guiding a surgical robot. Medical Imaging, IEEE Transactions on 1998;17(5):715-728.
Hamming et al., Automatic image-to-world registration based on x-ray projections in cone-beam CT-guided interventions. Med .Phys. May 2009;36(5):1800-1812.
Hayashibe et al., Surgical navigation display system using volume rendering of intraoperatively scanned CT images. Comput. Aided Surg, Sep. 2006;11(5):240-246.
Hofstetter et al., Fluoroscopy as en imaging means for computer-assisted surgical navigation, Comput.Aided Surg. 1999;4(465-76.
Jain et al., C-aim tracking and reconstruction without an external tracker. Med Image Comput Comput Assist Interv.2006;9(Pt 0:494-502.
Mitschke et al., Recovering the X-ray projection geometry for three-dimensional tornographie reconstruction with additional sensors' Attached camera versus external navigation system, Medical Image Analysis. 2003;7(I ):65-78.
Navab et al., Camera-augmented mobile C-arm (CAMC) application: reconstruction using a low-cost mobile c-atm, Med Image Comput Comput Assist Interv. 1999;688-697.
Navab et al., Merging visible and invisible: Two camera-augmented mobile C-arm (CAMC) applications, IEEE International Workshop on Augmented Reality, San Francisco, CA, USA 1999:134-141.
Navab et al., Visual serving for intraoperative positioning and repositioning of mobile C-arms. Med Image Comput Comput Assist Interv. 2006;9(Pt 0:551-60.
Otake et al., Development of a navigation system for femoral augmentation using an intraoperatie C-arm reconstruction. Proceedings of 9th Annual Meeting of CAOS-International, Boston, Jun. 2009:177-180.
Su et al., Augmented reality during robot-assisted laparoscopic partial nephrectomy: toward real-time 3D-CT to stereoscopic video registration. Urology Apr. 2009;73(4):896-900.
Wiesent et al., Enhanced 3-D-reconstruction algorithm for C-ann systems suitable for interventional procedures, IEEE Transactions on Medical Tmaging, 2000;19(5):391403.

* cited by examiner

SYSTEM AND METHOD FOR TRACKING AND NAVIGATION

CROSS-REFERENCE TO RELATED APPLICATION

This is a national stage application under 35 U.S.C. § 371 of PCT/US2012/035839 filed Apr. 30, 2012, the entire contents of which are incorporated herein by reference and this application claims the priority benefit under 35 U.S.C. § 119(e) of U.S. Provisional Application No. 61/480,422 filed Apr. 29, 2011, the entire contents of which are hereby incorporated by reference.

STATEMENT REGARDING FEDERALLY SPONSORED RESEARCH OR DEVELOPMENT

This invention was made with government support under Grant No. NIH R01-CA-127444, awarded by the National Institutes of Health (NIH). The government has certain rights in the invention.

BACKGROUND

1. Field of Invention

The field of the currently claimed embodiments of this invention generally relates to systems and methods for tracking and navigation such as, for example, in surgery, other image-guided interventions (e.g., radiation therapy), and other applications involving geometric registration of a physical (world) coordinate system and that of an image (or images).

2. Discussion of Related Art

In image-guided surgery, for example, surgical tools such as, for example, drills, surgical instruments, needles, and the like, as well as the patient, are generally tracked relative to a global (room) coordinate system by a six degrees-of-freedom (6 DOF) position tracking device (tracker) such as, for example, an optical tracker using multiple optical cameras. Intraoperative images taken, for example, using a mobile or ceiling- (or floor-) mounted C-arm imager, may also be obtained and registered to the room coordinate system. As depicted in FIG. 1, registration is conventionally achieved by mounting the tracker somewhere within the room and placing reference markers A, B, C, etc. (fiducials) on the tools as well as on the body of the C-arm imager to track the tools and C-arm externally.

Typical placement of the tracker device within the room, however, can often provide limited or interrupted line-of-sight for the tracker device during the procedure. This, in turn, risks diminished tracking accuracy as well as increased time in correctly aligning tracked elements, e.g., a C-arm, with respect to the table, the patient, etc.

What is needed is a tracking and navigation system with improved field-of-view and line-of-sight for the tracker as well as improved accuracy, ease of set up, alignment and calibration, and which has a reduced footprint.

SUMMARY

According to an embodiment, a tracking and navigation system is provided. The system may include an imaging or treatment device, a tracker device, and a fiducial marker. At least part of the imaging or treatment device may be movable relative to a patient. The tracker device may be mounted on the imaging or treatment device and may be movable therewith relative to the patient. The fiducial marker may be fixed to the patient to define a patient coordinate system. The fiducial marker may be detectable by the tracker device to substantially maintain registration between the tracker device and the patient coordinate system.

According to another embodiment, a tracking and navigation kit may be provided, including a tracker device and at least one fiducial marker. The tracker device may be configured for retrofitting to existing imaging or treatment devices, for example, to be mounted on an imaging or treatment device and movable therewith relative to a patient. The fiducial marker may be configured to be fixed to the patient to define a patient coordinate system. The fiducial marker may be detectable by the tracker device to substantially maintain registration between the tracker device and the patient coordinate system.

A novel tracking and navigation system is proposed. The system may include an "on-board" 6DOF tracker device such as, for example, a stereoscopic optical (e.g., infrared or visible light) camera, a stereoscopic video camera, and/or an electromagnetic or mechanical-based tracker, mounted onto the body of a C-arm or other imaging/therapy (treatment) device. Embodiments of the invention include a tracking and navigation system, a tracking device for retrofitting to existing tracking and navigation systems, and a calibration method for an on-board navigation system that enables the C-arm or other imaging/treatment device to track the external environment with respect to the coordinate system fixed to the C-arm itself. Embodiments of the invention may potentially eliminate the need for any external tracking device and may allow the imaging/treatment device to measure the external devices with respect to the dynamic reference frame (coordinate system) embedded to the C-arm itself. Alternatively, embodiments of the invention may be used in combination with conventional tracking embodiments (for example, placement of stationary trackers within the room). According to embodiments of the invention, problems related to line-of-sight and field-of-view of the tracker may be improved significantly. The system may allow a surgeon or another medical professional, for example, to more easily ensure the alignment of the target region in a center of the imager's field-of-view, and may also allow the tracker to track the target within its optimal field of view. Consequently, registration accuracy of the tracker may be improved and may also provide additional flexibility in navigation system design.

Furthermore, according to another embodiment, a video-based tracker may offer the additional benefit of easily providing the surgeon an augmented reality view by overlaying X-ray imaging and planning data, for example, onto the co-registered video image.

According to another embodiment, a method for system calibration may be provided which computes a relative transformation between the imaging device and the tracker.

Embodiments of the invention may solve general problems in image-guided therapy including, but not limited to, improved setup configuration of surgical apparati with superior field-of-view and line-of-sight for the tracker, improved tracking accuracy in image-guidance, reduced time in aligning the C-arm or other imaging/treatment device correctly with respect to the table and patient, and/or video augmentation in a streamlined configuration from a natural point of view.

Further features and advantages, as well as the structure and operation of various example embodiments of the invention, are described in detail below with reference to the accompanying drawings.

BRIEF DESCRIPTION OF THE DRAWINGS

The foregoing and other features and advantages of the invention will be apparent from the following, more particular description of some embodiments of the invention, as illustrated in the accompanying drawings. Unless otherwise indicated, the accompanying drawing figures are not to scale. Several embodiments of the invention will be described with respect to the following drawings, in which like reference numerals represent like features throughout the figures, and in which.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
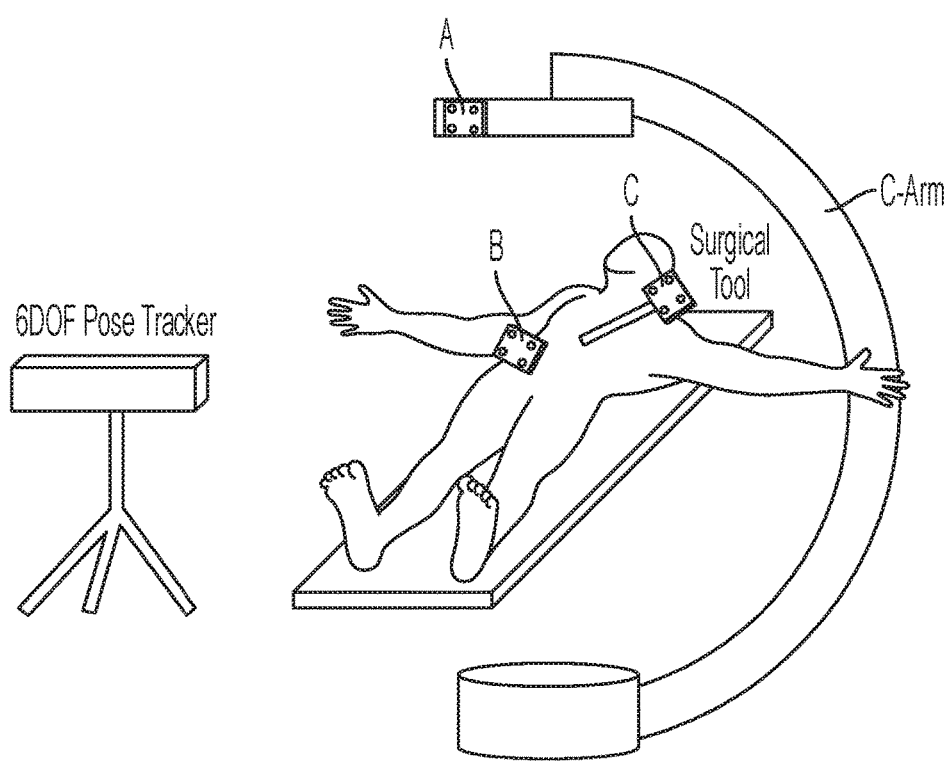
FIG. 1 is an illustrative perspective view of a conventional image-guided surgical navigation system including a pose tracker positioned within the operating theater.

FIG. 1 is an illustrative perspective view of a conventional image-guided surgical navigation system including a pose tracker positioned within the operating theater. As depicted in FIG. 1, registration is conventionally achieved by mounting the tracker somewhere within the room and placing reference markers A, B, and C on the body of the C-arm imager, on the patient, and on the tools, respectively.

Figure 2:
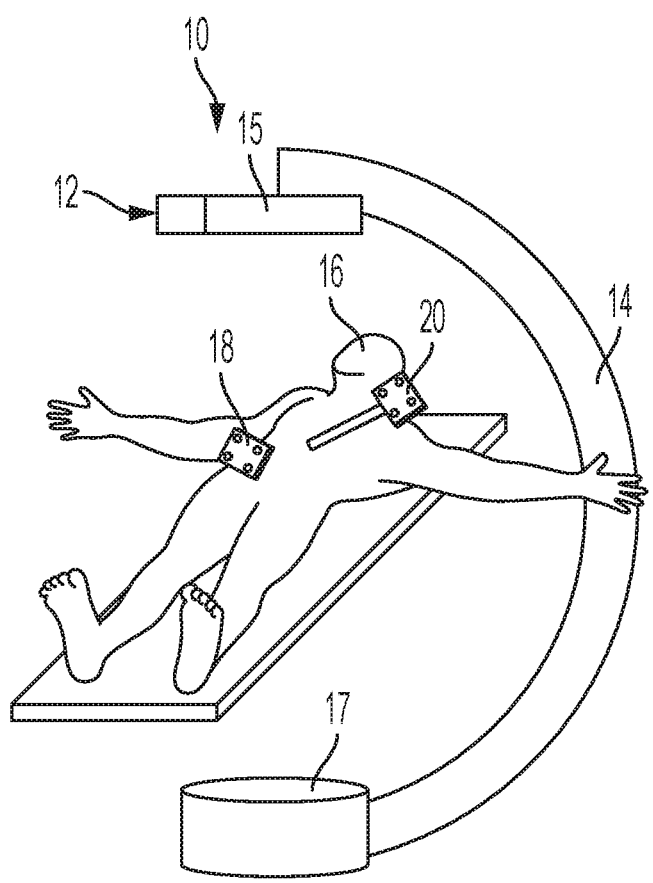
FIG. 2 is an illustrative perspective view of a surgical tracking and navigation system having an "on-board" tracker device mounted on a moveable imaging or treatment device according to an embodiment of the invention.

FIG. 2 depicts an illustrative perspective view of a surgical tracking and navigation system 10 having an "on-board" tracking device 12 mounted on a moveable portion of an imaging or treatment device 14 according to an embodiment of the invention. At least part of the imaging or treatment device 14 is movable relative to a patient 16 and the tracker device 12 is movable therewith relative to the patient 16. A fiducial marker 18 may be fixed to the patient 16 to define a patient coordinate system. The fiducial marker 18 may be detectable by the tracker device 12 to substantially maintain registration between the tracker device 12 and the patient coordinate system.

The imaging or treatment device 14 depicted in FIG. 2 is shown schematically as a C-arm but may be any number of imaging or therapeutic devices such as, for example but not limited to, a mobile C-arm for 2D radiographic imagery, fluoroscopy or 3D cone-beam computed tomography (CBCT), a ceiling-, floor-, or wall-mounted C-arm for 2D radiographic imagery, fluoroscopy or CBCT, a table-integrated radiography/fluoroscopy system, a radiation therapy linear accelerator, a robotic radiotherapy device, a radiotherapy simulator, or a combination of these. The mobile C-arm may be, for example but not limited to, a PowerMobil C-arm, available from Siemens Healthcare, Erangen, Germany. Alternatively, the device 14 may be in the form of a U-arm (e.g., xCAT® ENT from Xoran Technolgies®, Inc. of Ann Arbor, Mich.), an O-arm (e.g., from Medtronic, Inc. of Minneapolis, Minn.), or another movable arm. In an embodiment, the tracker device 12 may be mounted to (or proximate to) an image receptor 15 of the imaging or treatment device 14. According to another embodiment, the tracker device 12 may be mounted to a surgeon or other medical professional moving relative to the patient 16, in which case the surgeon may be considered to be the imaging or treatment device 14.

The tracker device 12 may be, for example, but not limited to, a stereoscopic optical tracker (e.g., infrared or visible light based), a stereoscopic video-based tracker, an electromagnetic tracker, a mechanical link-based tracker, a structured-light or laser-based surface scanner, or a combination thereof which may provide 6DOF position of tools with respect to a common coordinate system. Generally speaking, a tracking system (one or more tracker devices) may measure/detect the physical position of one or more reference markers (fiducials) in real-time. Affixing multiple markers in known arrangements to surgical tools and other structures to be tracked allows real-time measurement of pose in the world (tracker) reference frame. The pose of the markers is defined by the position and orientation, represented by, for example, six independent variables (six degrees of freedom): three translational coordinates and three rotational angles. Currently available tracker technologies include mechanical, electromagnetic (EM), and optical- and video-based tracking systems. The tracker device may also utilize, alone or in combination with the foregoing tracker devices, a structured-light or laser-based surface scanning system to map a 3D surface within the field of view.

An electromagnetic (EM) tracker typically includes a field generator (FG) to produce a low-frequency EM field and a receiver with one or more sensor coils. The position and orientation of the receiver with respect to the FG are determined based on the measurement of the sensor coil and calibrated dependence on the EM field. A disadvantage of EM trackers is the sensitivity to field distortions imparted by surrounding devices (e.g., power generators, monitors, and metallic devices within the field of measurement). Metallic materials distort the EM field. A significant advantage of EM trackers is the freedom from line-of-sight between the FG and the sensors, allowing tracking of small sensor coils inserted in needles or catheters inside the body. An example EM tracking system is the NDI Aurora (Northern Digital Inc., ON, Canada).

A mechanical localizer employs an articulated arm whose tip position with respect to a known base frame can be determined from the angles of joints using forward kinematics. Articulated arms are highly accurate, reliable, and stable but unable to track multiple devices concurrently and are cumbersome to use and position. They are therefore rarely used in modern surgical navigation. The FARO surgical arm (FARO Medical Technologies, FL, USA) is an example of such technology.

Optical trackers compute the pose of optical markers from 2D stereoscopic images using epipolar geometry. Optical trackers may fall into two main categories—those using active and passive markers. Active systems track light-emitting markers, usually infrared light-emitting diodes (LEDs, e.g., Optotrak, Northern Digital Inc., Mississagua ON, Canada). Passive systems are usually classified as infrared (IR)-based or optical video-based trackers. The passive IR-based trackers equipped with light-emitting sensors flash light from a ring surrounding each camera lens to localize retro-reflective markers (e.g., Polaris Spectra and Vicra, Northern Digital Inc. ON, Canada). Both active and passive IR-based systems require the markers to be observed as bright spots over a dark background. Video-based trackers generally use a stereoscopic camera pair to observe passive targets with specific geometric patterns (e.g., MicronTracker from Claron Technology Inc., Toronto ON, Canada). Optical trackers are the most prevalent tracking systems used for image-guided surgery due to their relatively large field of view and high accuracy compared to, for example, EM systems. A significant drawback of optical trackers is the direct line-of-sight requirement. Additionally, a common limitation faced by both EM and optical trackers is signal degradation when the trackers are positioned at a distance from the targets, potentially reducing geometric accuracy in tracker measurement.

Figure 3A:
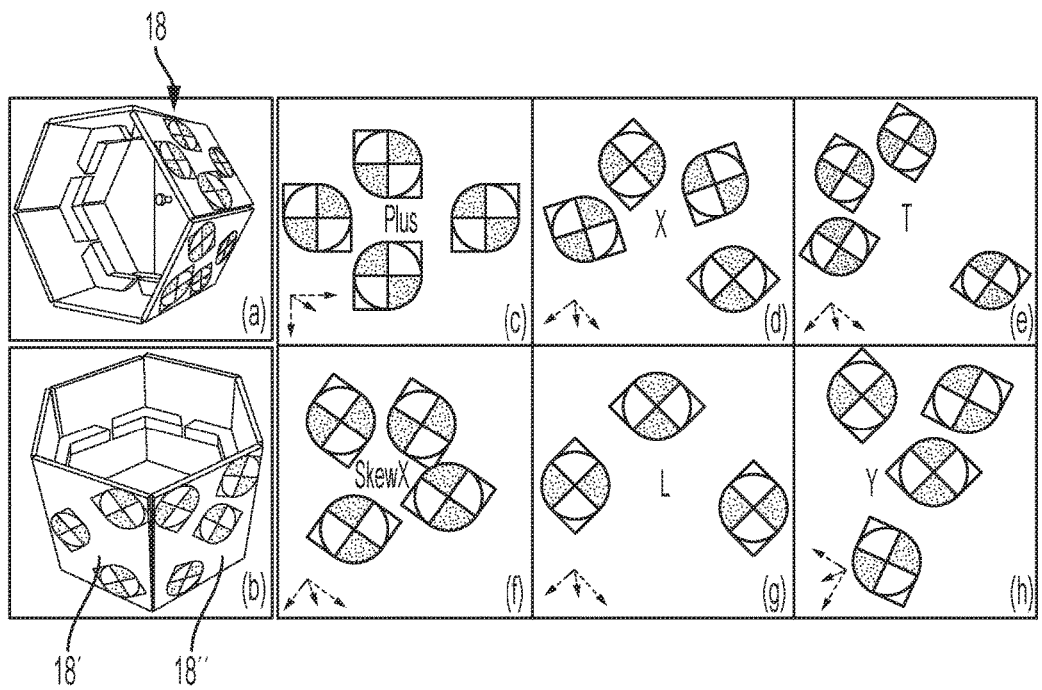
FIG. 3A depicts multiple views of a fiducial marker according to an embodiment of the invention, the marker configured to be detected by an optical- or video-based tracking device.

FIG. 3A depicts multiple views of a novel reference marker 18 (fiducial) configured to be detected by an optical- or video-based tracking device according to an embodiment of the invention. The reference marker 18 (fiducial) may be used to define a coordinate system associated rigidly with the patient so that intraoperative tracking can be accomplished relative to the patient coordinate system rather than the coordinate system associated with the tracker 12. This may eliminate measurement errors due to motion of the tracker.

According to the embodiment shown in FIG. 3A, the marker 18 may include a plurality of faces 18', 18", etc. having black-and-white checkerboard-like patterns thereon, referred to as X-points (e.g., provided by Claron Technology, Inc.). X-lines denote the two imaginary straight lines crossing at the center of an X-point. The X-lines connecting two X-points form a vector. The vector points from the center of one X-point to the center of the other X-point. According to an embodiment, one vector must be at least 2 mm longer than the other, and an angle between the two vectors must be in the range 8°-172°. Two vectors on the same plane form a marker facet; therefore, in an embodiment, each marker facet must contain at least 3-4 X-points. A marker 18 may contain one or more facets in rigid configuration. The description of the marker geometry may be stored in a marker template file, and unique description of the marker geometry may allow marker recognition and pose measurement by the tracker 12. Each facet 18', 18" may have its own coordinate system, with the origin at the middle of the longer vector. The x-axis extends from the origin toward the head of the longer vector. The z-axis is parallel to the cross product of the long and short vector but points in the opposite direction. The y-axis is defined according to the right-hand coordinate system rule. To maximize angular accuracy, at least two X-points on a facet should be placed as far as possible from each other. Marker surfaces on which X-points are laid should be flat, although X-points on a slightly curved surface may still be detectable (but subject to pose measurement errors). As shown in the embodiment depicted in FIG. 3A, the marker 18 may be a hex-face reference marker for the tracker 12, although markers with a different number of faces, e.g., one or more faces, is possible. The hex-face reference marker 18 may include includes six faces 18', 18", etc. attached, for example, to six acrylic planar surfaces aligned in a hexahedral shape and visible from 360° to define the patient coordinate system and maintain tracker-to-patient registration.

Figure 3B:
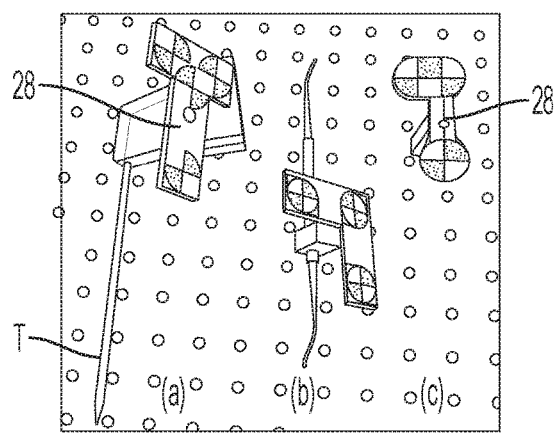
FIG. 3B depicts a perspective view of a plurality of surgical tools having another fiducial marker affixed thereto for detection by an optical- or video-based tracker device according to an embodiment of the invention.

FIG. 3B depicts a perspective view of a plurality of surgical tools T having another fiducial marker 28 affixed thereto for detection by an optical- or video-based tracker device 12 according to an embodiment of the invention. Real-time visualization of surgical instruments (e.g., pointers, suctions, drills, and endoscopes) with respect to images or planning data in image-guided surgery assists the surgeon in achieving precise approach and excision/ablation of a surgical target while respecting surrounding normal tissues. Typical tracking systems localize specific markers mounted on or integrated into various surgical instruments (e.g., pointers). EM trackers, for example, report the position and orientation of sensor coils embodied into the tooltip. IR-based optical trackers, on the other hand, localize IR-emitting or retro-reflective markers attached to the tool handle. According to the embodiment depicted in FIG. 3B, video-based trackers measure the pose of specific markers 28 (e.g., X-points) attached to the tool T. For the optical tracking systems, a pivot calibration may be used to estimate the tooltip position relative to the coordinate system of the marker 28 attached to the tool handle. The pivot calibration may be performed to find the least-squares solution to the tip position with respect to the tool marker 28. The tool markers 28 generally follow the design considerations detailed above for the reference marker 18. In addition, the x-axis of the marker 28 is placed along the tool T, and the angle between the two vectors defining the marker facet may exceed 8°.

Embodiments of the invention include a system and a calibration method for an "On-Board" surgical navigation system that enables a tracker provided on the imaging or treatment device to track the external environment with respect to the coordinate system associated with the imaging or treatment device. The system may eliminate the need for (but not preclude the use of) an externally located tracking device and may allow the imaging or treatment device to measure the external devices with respect to the dynamic reference frame embedded to the imaging and treatment device. According to embodiment of the system, known problems concerning line-of-sight and field of view of the tracker may be improved significantly or even resolved. The system may allow a surgeon to, for example, easily ensure the alignment of the target region in the center of the imager's field of view, and it also allows the tracker to track the target within its optimal field of view. Consequently, the system may improve the registration accuracy and provide flexibility in navigation system design. Additionally, in an embodiment including a video-based tracker, an additional benefit may be that a surgeon may be able to obtain an augmented reality view by overlaying the X-ray imaging and planning data onto the co-registered video image. A method for system calibration which computes a relative transformation between the imaging or treatment device and the tracker may also be provided.

Embodiments of the invention may solve known problems by mounting the tracker 12 on the body of the imager or treatment device 14 (e.g., C-arm or radiation therapy system linear accelerator gantry) and registering it with the X-ray imager preoperatively. The system 10 does not preclude the use of additional in-room trackers mounted within the room to track the position of the imaging system and 'on-board' tracker. Such known problems and the associated advantages of the 'on-board' tracker are summarized below:

1) Superior configuration of surgical apparati due to the FOV and line-of-sight of the tracker. All types of trackers have a certain range of field of measurement which is typically 1.0-3.0 m for optical trackers, and 0.5 m for electro-magnetic tracker. In the case of an optical tracker, the target marker should not be occluded by any other apparatuses in order to ensure the "line-of-sight" from the tracker. For these limitations, the configuration of several apparati in the operating theater such as anesthesia controller, endoscopic monitors, light booms, etc. are restricted. According to embodiments of the invention, however, the system 10 does not require any external tracking device, so these limitations may be eliminated and the overall system becomes more compact. Other surgical apparati can be placed around the imaging or treatment device 14 which gives surgical staff flexibility, and the tracking system is unobtrusive to the operating theater configuration.

2) Improved tracking accuracy may be obtained due to the characteristics and placement of the tracker 12. In conventional tracker configurations, in order to assure the line-of-sight and track all the tracker markers from one tracker, the tracker has to be located at about 2.0-3.0 m distance from the surgical field, which is not the optimal distance for many types of trackers. As a result, the accuracy of image guidance deteriorates. In embodiments of the surgical tracking and navigation system, a patient reference marker 18 (fiducial) and a surgical tool fiducial 20 may be provided. Therefore, the distance from the tracker 12 to the tracked object (for example the patient and/or tracked apparati) can be made shorter which may increase tracking accuracy.

3) Improved time and workflow in setup of the imaging or treatment device. For example, one of the difficulties of using a conventional tracking system and C-arm in an operation is to setup the device itself to the optimum position with respect to the position and operating table. One factor that should be considered in this process is the field of view. Generally, the field of view of the C-arm is not apparent from the body shape. Hence, the surgeon often adjusts the position while exposing X-rays several times so that the target organs are within the field of view. Additionally, in the case of mobile C-arm CT, external factors can interfere with CT acquisition (such as a collision between the C-arm and the patient bed during the scan, metallic artifact due to surrounding metallic parts, etc.) should also be taken into account during this process. Therefore, this setup process takes time and is a major bottleneck in the surgical workflow of current C-arm image-based surgical navigation. According to embodiments of the invention, however, the field of view of the imaging or treatment device 14 in the real world can be tracked in real-time using the mounted tracker 12. Furthermore, when a video-based tracker 12 is used, for example, the field of view may be visualized overlaid onto the video image in real-time. Consequently, the setup time should be significantly reduced and, at the same time, the amount of X-ray exposure during this targeting process should be also reduced.

4) Natural video perspective on the patient. Since the tracker 12 is mounted 'on-board' the imaging or treatment device 14 according to embodiments, and because these systems are usually positioned in proximity to the patient 16 with a pertinent perspective on the scene, an 'on-board' video-based tracker naturally provides a useful perspective of the patient 16. For example, as shown in FIG. 2, a C-arm 14 may be "parked" with the image receptor 15 directly over the patient 16, such that the video-based tracker 12 looks directly down upon the patient 16 (on the surgical scene). Likewise, imaging or treatment device 14 may be a radiotherapy linear accelerator oriented so as to deliver a high-energy radiation beam to a target from specific, planned orientations about the patient 16, and an 'on-board' video-based tracker 12 may provide a natural, meaningful perspective from these views. Other systems for video augmentation use a video camera (not a video-based tracker) on a separate arm or mount that is either fixed in the room (limiting the useful perspective) or brought to table-side in a manner that can be obtrusive to the procedure.

5) Lack of obtrusiveness. Because the 'on-board' tracker device is mounted directly on the C-arm or other imaging device, it may not occupy any extra 'footprint' within the operating theatre and therefore may not interfere with other infrastructure at table-side—e.g., other equipment, booms, and surgical staff. Other tracking systems may be brought close to tableside to reduce line-of-sight limitations and/or improve tracker accuracy—e.g., an electromagnetic tracker suspended on a linked armature over the patient—and are comparatively intrusive.

Example: System Calibration Method

Figure 5:
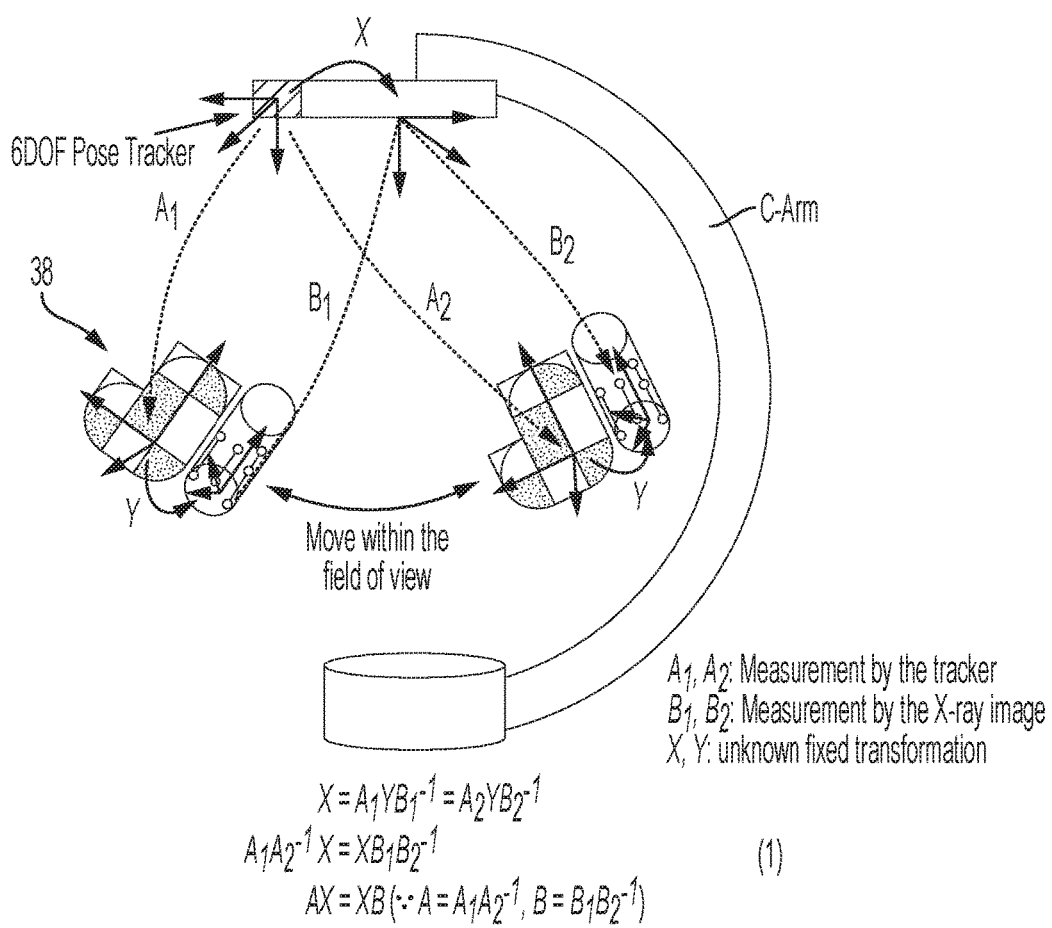
FIG. 5 depicts a calibration process for the surgical tracking and navigation system according to an embodiment of the invention.

In an embodiment, a calibration method of the inventive system is provided. FIG. 5 depicts a calibration process for the surgical tracking and navigation system 10 according to an embodiment of the invention. A goal of the calibration is to compute the relative transformation between the tracker coordinate system and the imaging or treatment device coordinate system which is typically assumed on the detector plane. The calibration may enable the system to integrate these two coordinate systems and make the measured pose interchangeable between these two systems. Since the tracker 12 can be rigidly mounted onto the body of the C-arm 14 (or other relevant imaging or therapy device), the calibration should be done once in a certain period (e.g. a few months). This may make the intraoperative workflow simpler, rather than doing it intraoperatively as implemented in some conventional systems. The calibration method proposed here is just one example which provides the transformation with reasonable accuracy using easily attainable conventional devices.

Figure 4:
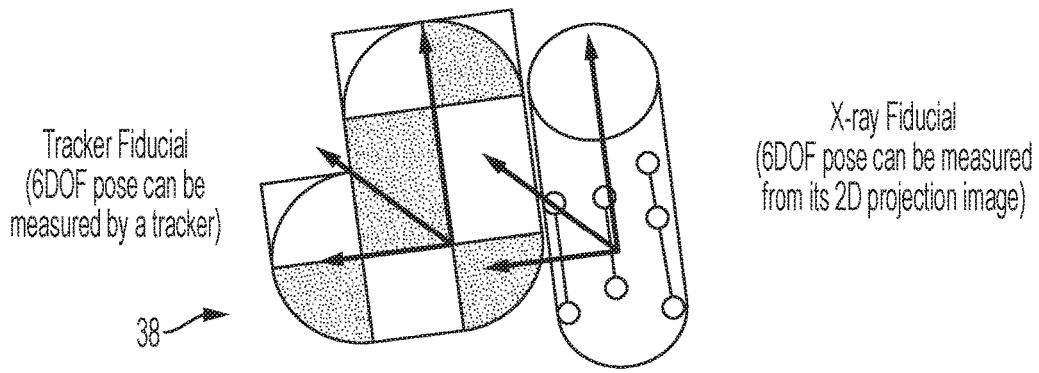
FIG. 4 depicts a fiducial tool for calibration of a surgical tracking and navigation system according to an embodiment of the invention.

In one embodiment shown in FIG. 4, the calibration uses a calibration fiducial 38 including a tracker fiducial and an X-ray fiducial. Typically, the tracker fiducial 38 is composed of infrared reflective plastic spheres, black and white checker pattern, or an electro-magnetic coil. The X-ray fiducial may contain some type of radioopaque features (e.g. metallic beads, wires, ellipses, etc.) in a known configuration and which enables estimation of its 6DOF pose with respect to the imager coordinate system from its 2D projection image. The calibration process using the calibration fiducial 38 is shown in FIG. 5. The pose of the tracker fiducial with respect to the tracker 12 and the X-ray fiducial with respect to the C-arm 14 can be measured simultaneously by the tracker and an X-ray image (A1 and B1 in FIG. 5). The measurement may be repeated several times while the calibration fiducial 38 is moved randomly. By using these data and equation (1)—see FIG. 5—the transformation between the tracker coordinate and the C-arm coordinate (X) can be estimated by solving AX=XB problem in a least-square sense which is a well understood calibration calculation.

Example: Video Augmentation and Virtual Fluoroscopy

According to an embodiment, and referring back to FIG. 2, utilization of an "on-board" tracker device 12 (e.g., on the gantry of a linear accelerator) may provide additional tracking capabilities and may also allow visualization/video augmentation of the patient 16 and region to be treated in the dynamic reference frame of, for example, a radiotherapy delivery system. Tracking capability could include monitoring of patient motion, breathing, etc. Video augmentation capability could include a direct image of the patient from the perspective of the treatment device, augmented by overlay of various imaging and/or treatment planning information.

Direct mounting of a surgical tracker 12 on a rotational C-arm 14 (or other imaging or therapy device) offers potential performance and functional advantages in comparison to a conventional in-room tracking configuration. Key functionality implemented on the system includes tracking, virtual fluoroscopy, and video augmentation. The hex-face reference marker demonstrates capability to maintain registration in a dynamic reference frame, e.g., across a full C-arm range of rotation and, by virtue of its perspective over the operating table, may reduce line-of-sight obstruction commonly attributed to occlusion of the tracker view by personnel about tableside. While one embodiment used a hex-face marker in which (during C-arm rotation) the face presenting the least obliqueness to the tracker was used for registration, alternative methods such as using as many faces as visible for any pose measurement are also possible.

The reference marker 18 thereby maintains tracking capability (as well as virtual fluoroscopy, video augmentation, etc.) as the C-arm 14 rotates about the table for fluoroscopy or CBCT—as long as the reference marker 18 is within its FOV. This implies, of course, that the system may only be functional when the C-arm remains at tableside (as common in fluoroscopically guided procedures) with the reference marker 18 in the FOV. This may be consistent with workflow and logistics of many minimally invasive procedures that utilize fluoroscopy throughout the operation (e.g., minimally invasive spine surgery), but for procedures in which a C-arm is used only intermittently and then pushed aside (e.g., skull base surgery), such capabilities would only be available when the C-arm is at tableside. Thus, a combined tracker arrangement utilizing, for example, a conventional tracker configuration to allow surgical navigation throughout the procedure and which is augmented by the C-arm mounted tracker device 12 when the C-arm is at tableside, giving added capability for tracking (at higher geometric accuracy by virtue of two trackers), virtual fluoroscopy, and video augmentation.

Real-time DRR capabilities made possible by the system may also assist the surgeon in C-arm setup and radiographic search/localization of target anatomy without x-ray exposure. Such functionality could reduce fluoroscopy time expended in tasks such as vertebral level counting/localization, selection of specific PA/LAT/oblique views, and aligning the C-arm at tableside. With the increasing concern regarding radiation exposure to physicians, such technology may provide opportunity for improving OR safety. The system may be useful in assisting anatomical localization and level counting, and virtual fluoroscopy may assist positioning the C-arm to achieve a desired x-ray perspective prior to radiation exposure. Virtual fluoroscopy may be helpful, for example, in precisely aligning the C-arm to acquire the desired perspectives. Virtual fluoroscopy may therefore provide speed and reduce radiation exposure in "hunting" for complex oblique views of specific anatomical features, such as the "bullseye" view for transpedicle needle insertion and localization of the tip of the humerus as an entry point for humeral nail insertion. Since virtual fluoroscopy can be computed from either preoperative CT or intraoperative CBCT (typically the former), it can be used even in complex patient setups that challenge or prohibit 180° rotation of the C-arm for CBCT acquisition—for example, the lithotomy position in prostate brachytherapy and the "beach-chair" position in shoulder surgery.

The video-based tracker used in the current work may allow video-augmentation from a natural perspective (surgeon's-eye-view) over the operating table. Overlay of a virtual field light may assist in positioning the C-arm to align the CBCT FOV to the target region without x-ray exposure. Overlay of DRRs and pre-operative planning and/or image data onto the video stream may provide intuitive visual localization of surgical tools with respect to images and/or planning structures. Rigid fixation of the tracker with respect to the x-ray detector may facilitate quick, accurate intraoperative registration using the tracker-to-detector transformation and geometric calibration of the C-arm. The proposed configuration may present streamlined integration of C-arm CBCT with real-time tracking and demonstrated potential utility in a spectrum of image-guided interventions (e.g., spine surgery) that could benefit from improved accuracy, enhanced visualization, and reduced radiation exposure. Video augmentation may show potential value in minimally invasive spine surgery by allowing the surgeon to localize target anatomy relative to the patient's skin surface. Planning data overlay may facilitate quick localization of target tissues and margins. DRR overlay on real-time video may assist, for example, in vertebral level counting and localization by showing anatomical structures with respect to the skin surface of the patient.

The embodiments illustrated and discussed in this specification are intended only to teach those skilled in the how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A tracking and navigation system, comprising:
an imaging or treatment device, wherein at least part of the imaging or treatment device is movable relative to a patient;
a tracker device mounted on the imaging or treatment device and movable therewith relative to the patient; and
a fiducial marker configured to be fixed relative to the patient to define a position and orientation of a patient coordinate system relative to a coordinate system of the tracker device, the fiducial marker having a polyhedral structure having a plurality of faces, each face being connected to at least two neighboring faces, each face having a plurality of marks defining a three dimensional coordinate system with an origin point and first and second axes within each face and a third axis that is perpendicular to the first and second axes, each face having marks that are distinguishable from marks on other faces of the polyhedral structure,
wherein the fiducial marker is configured and arranged to be detected by the tracker device to substantially maintain six-degree-of-freedom registration between the patient coordinate system and the coordinate system of the tracker device, and wherein the tracker device is configured to:
   detect the plurality of marks on at least one face of the fiducial marker, and
   determine a position and an orientation of the patient coordinate system relative to the coordinate system of the tracker device in six degrees of freedom based upon the marks on each face and based upon the three dimensional coordinate system defined by the plurality of marks on the at least one face of the fiducial marker detected by the tracker device.

2. The tracking and navigation system according to claim 1, wherein the imaging or treatment device is mobile.

3. The tracking and navigation system according to claim 2, wherein the imaging or treatment device is equipped to perform fluoroscopy, cone-beam computed tomography (CBCT), x-ray radiography, radiation therapy, robotic radiotherapy, radiotherapy simulation, or a combination thereof.

4. The tracking and navigation system according to claim 2, wherein the imaging or treatment device comprises a C-arm.

5. The tracking and navigation system according to claim 1, wherein the imaging or treatment device is mounted to a floor, ceiling, or wall in a room.

6. The tracking and navigation system according to claim 5, wherein the imaging or treatment device is equipped to perform fluoroscopy, cone-beam computed tomography (CBCT), x-ray radiography, radiation therapy, robotic radiotherapy, radiotherapy simulation, or a combination thereof.

7. The tracking and navigation system according to claim 5, wherein the imaging or treatment device comprises a C-arm.

8. The tracking and navigation system according to claim 1, wherein the tracker device comprises a stereoscopic optical-based tracker, a stereoscopic video-based tracker, an electromagnetic field-based tracker, a mechanical-based tracker, a structured-light or laser-based surface scanner, or a combination thereof.

9. The tracking and navigation system according to claim 1, wherein the tracker device comprises a stereoscopic optical-based tracker or a stereoscopic video-based tracker, and wherein on each face, the plurality of marks form a two-tone checker pattern.

10. The tracking and navigation system according to claim 1, wherein the polyhedral structure is a hexahedron and wherein the plurality of faces comprise six faces, each face being arranged to be visible by the tracker device in an angular range so that the six faces are visible from 360 degrees when viewed sequentially.

11. The tracking and navigation system according to claim 1, further comprising a second fiducial marker affixed to a surgical tool.

12. The tracking and navigation system according to claim 11, wherein the tracker device comprises a stereoscopic optical-based tracker or a stereoscopic video-based tracker, and wherein the second fiducial marker comprises a two-tone checker pattern.

13. A tracking and navigation kit for use with an imaging or treatment device, comprising:
   a tracker device configured to be mounted on the imaging or treatment device and movable therewith relative to a patient; and
   a fiducial marker configured to be fixed relative to the patient to define a position and orientation of a patient coordinate system relative to a coordinate system of the tracker device, the fiducial marker having a polyhedral structure having a plurality of faces, each face being connected to at least two neighboring faces, each face having a plurality of marks defining a three dimensional coordinate system with an origin point and first and second axes within each face and a third axis that is perpendicular to the first and second axes, each face having marks that are distinguishable from marks on other faces of the polyhedral structure, wherein the fiducial marker is detectable by the tracker device to substantially maintain six-degree-of-freedom registration between the patient coordinate system and the coordinate system of the tracker device, and wherein the tracker device is configured to:
   detect the plurality of marks on at least one face of the fiducial marker, and
   determine a position and an orientation of the patient coordinate system relative to the coordinate system of the tracker device in six degrees of freedom based upon the marks on each face and based upon the three dimensional coordinate system defined by the plurality of marks on the at least one face of the fiducial marker detected by the tracker device.

14. The tracking and navigation kit according to claim 13, wherein the tracker device comprises a stereoscopic optical-based tracker, a stereoscopic video-based tracker, an electromagnetic field-based tracker, a mechanical-based tracker, a structured-light or laser-based surface scanner, or any combination thereof.

15. The tracking and navigation kit according to claim 13, wherein the tracker device comprises a stereoscopic optical-based tracker or a stereoscopic video-based tracker, and wherein on each face, the plurality of marks form a two-tone checker pattern.

16. The tracking and navigation kit according to claim 13, wherein the polyhedral structure is a hexahedron and wherein the plurality of faces comprise six faces, each face being arranged to be visible by the tracker device in an angular range so that the six faces are visible from 360 degrees when viewed sequentially.

17. The tracking and navigation kit according to claim 13, further comprising a second fiducial marker configured to be affixed to a surgical tool and detectable by the tracker device.

18. A fiducial marker configured to provide six-degree-of-freedom information to a tracking system associated with at least one of an imaging or treatment device, the fiducial marker comprising:
   a polyhedral body having a plurality of substantially flat faces, each face being connected to at least two neighboring faces, and
   a plurality of marks on each face, the plurality of marks defining a three dimensional coordinate system with an origin point and first and second axes within each face and a third axis that is perpendicular to the first and second axes, the plurality of marks on each face being distinguishable from marks on other faces of the polyhedral body,
   wherein a first face in said plurality of faces has a first pattern, the first pattern being detectable by said tracking system,
   wherein said first pattern has marks structured to provide information to said tracking system to define six degrees of freedom including position and orientation of a coordinate system associated with said fiducial marker relative to a coordinate system associated with the imaging or treatment device or both.

19. The fiducial marker of claim 18, wherein a second face in said plurality of faces has a second pattern, the second pattern being detectable by said tracking device.

20. The fiducial marker of claim 19, wherein said second pattern has marks structured to provide information to said tracking device to define six degrees of freedom including position and orientation of a coordinate system associated with said fiducial marker.

* * * * *